United States Patent [19]
Teeple

[11] Patent Number: 4,635,625
[45] Date of Patent: Jan. 13, 1987

[54] SURGICAL EYE MASK

[76] Inventor: Edward Teeple, 641 Ridgefield Ave., Mt. Lebanon, Pa. 15216

[21] Appl. No.: 661,120

[22] Filed: Oct. 15, 1984

[51] Int. Cl.$^4$ .............................................. A61F 13/12
[52] U.S. Cl. ......................................... 128/163; 2/15
[58] Field of Search ............... 128/163, 132 R, 156; 2/15, 9

[56] References Cited

U.S. PATENT DOCUMENTS

| | | | |
|---|---|---|---|
| 2,165,668 | 7/1939 | Vaccaro | 128/163 UX |
| 2,543,104 | 2/1951 | Golding | 128/163 |
| 2,572,638 | 10/1951 | Loos | 128/163 |
| 2,874,385 | 2/1959 | Wade | 128/163 X |
| 3,814,095 | 6/1974 | Lubens | 128/156 X |
| 4,331,136 | 5/1982 | Russell et al. | 128/163 |

Primary Examiner—Mickey Yu
Attorney, Agent, or Firm—Reed Smith Shaw & McClay

[57] ABSTRACT

A surgical eye mask for use during laser treatment having a facial member made from a metal foil on which a pair of eye pads are secured to contact the patient's eyelids during use. An adhesive is positioned about the periphery of the mask to provide a temporary seal against laser irradiation.

3 Claims, 3 Drawing Figures

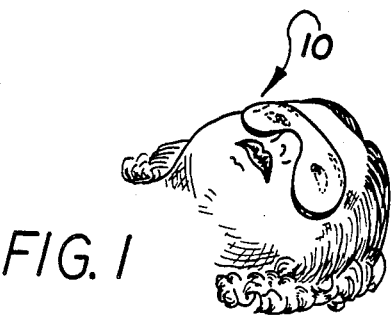
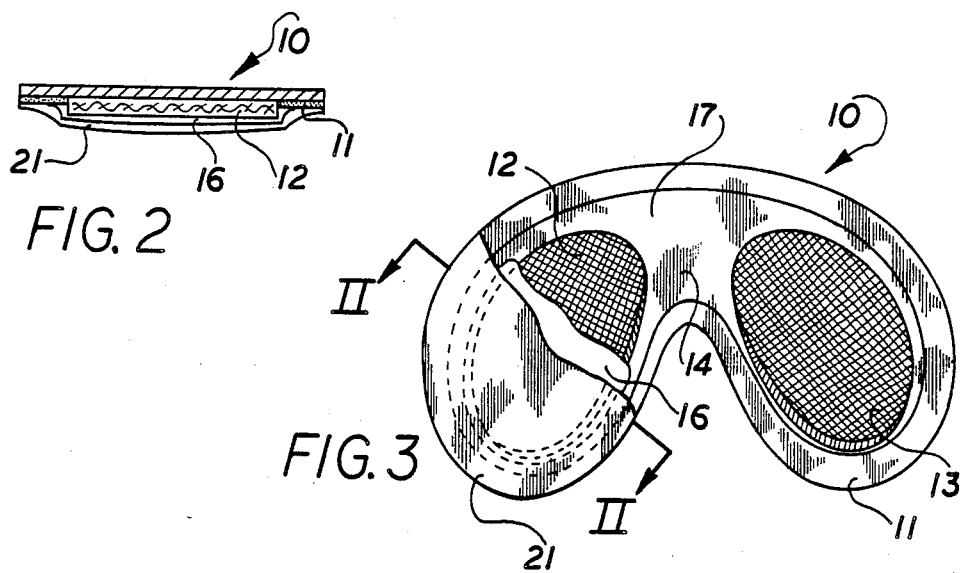

SURGICAL EYE MASK

FIELD OF THE INVENTION

The present invention relates to a surgical eye mask and, in particular, to an eye mask for use during surgical procedures in which a laser is used.

BACKGROUND OF THE INVENTION

In recent years the use of lasers for medical procedures has become more common. Many of these procedures use laser devices as a surgical scalpel to perform precise and delicate incissions. These devices have also been used in other types of procedures, but their principal application to date has been surgical.

Notwithstanding the many advantages of laser tools, they present a number of dangers in the operating room. The most prevalent danger is from divergent or scattered radiation. The coherent beam from most devices used in the operating room is of sufficient power to cause skin burn and eye damage from scattered or reflected beams. Normally, operating room personnel wear protective clothing and specially made goggles or eye glasses to protect themselves from stray radiation.

Patients undergoing such treatment or surgical procedures are covered in protective garments which provide a degree of protection. Also, eyes and face are covered with gauze to protect them from the stray radiation. However, most of the facial and, in particular, the eye protection is not adequate. In the case of eye protection, stray radiation finds its way in through the gauze at the bridge of the nose or around the nose and cheekbone areas. A further disadvantage is that the tape and petroleum based eye lubricants commonly used are potentially ignitable by stray irradiation.

Accordingly, it is an object of the present invention to provide an eye mask which will afford a patient undergoing laser surgery or therapy complete protection from stray or divergent laser radiation. It is a further object of the invention to provide an eye mask which will prevent the eyes from drying out during the procedure during which the mask is being used.

SUMMARY OF THE INVENTION

Generally, the present invention provides a mask shaped and contoured to cover the patient's eyes including the area above the patient's eyebrows, bridge of the nose, and cheekbones. The periphery of the mask includes a continuous adhesive to provide a temporary seal around the periphery of the mask and the facial skin of the patient. The seal precludes the ingress of divergent laser radiation.

The outer surface of the mask is made of a highly reflective metal foil, preferably aluminum. The inner surface of the mask, i.e., inwardly of the continuous adhesive strip, is provided with a pair of adsorptive pads, such as cotton or cotton gauze, which contains or is adapted to contain a moistening fluid, such as a saline solution to maintain the eye moisture during surgery or other laser procedures. Positioned over the adsorptive eye pads is a waterproof material, such as waxed paper, when it is desired to pre-moisten the mask. In such case, the moisture proof material encompasses the entire adsorptive material and includes an adhesive perimeter to sealingly secure it to the inner surface of the mask foil and to keep the moisture in the adsorptive material from evaporating.

Preferably, a backing material is positioned over the entire back of the foil mask. It is desirable that the backing be made of a material which is easily stripable from the adhesive on the periphery of the mask, such as a resin coated paper. The backing material affords protection to the mask in its unused state. It is also possible to use a front protective sheet to protect the metal foil comprising the front or outer surface of the mask.

When the mask of the present invention is desired for use, the backing is removed from the mask as well as the waterproof material over the adsorptive pads. The mask is then positioned over the eyes of the patient and the periphery of the mask pressed against the skin to create a seal. Other advantages of the invention will become apparent from a perusal of the following detailed description of a presently preferred embodiment taken in connection with the accompanying drawings.

BRIEF DESCRIPTION OF THE DRAWINGS

FIG. 1 is a perspective view of the mask of the present invention attached to the face of the patient;

FIG. 2 is a sectional elevation taken along line 2—2 of FIG. 3; and

FIG. 3 is a perspective view of the inner surfaces of the mask.

PRESENTLY PREFERRED EMBODIMENT

With reference to the drawings, mask 10 of the present invention is adapted to sealingly fit over the eyes of a patient. Mask 10 is preferably made from a metal foil such a aluminum and cut to conform to the outline of the patient's eye cavity including the area above the eyebrows and below the cheekbones as shown in FIG. 1.

Referring to FIG. 3, the inner surface 17 of mask 10 includes an adhesive 11 positioned around the periphery of the mask. Adhesive 11 is preferably designed for temporary adhesion to the skin. A pair of absorptive eye pads 12 and 13 are positioned on inner surface of mask 10 and separated by nose bridge 14. Eye pads 12 and 13 are preferably made from a cotton gauze to retain a moistening solution during the operation or procedure. Normally, a saline solution is used as the moistening fluid.

The fluid can be added just prior to use or can be added at the time of manufacture. In the latter case, a nonwettable cover 16 is positioned over both pads and stripably secured to the mask's back surface 17. These covers are removed immediately before use.

It is also preferred to include covers 21 over back surface 17 which is peelably secured thereto by means of adhesive 11. A resin coated paper may be used to permit the cover to easily peel off the mask at the time of use. Cover 21 protects the mask from the time of manufacture to use. However, it is clear that such a cover is not required; and stacks of masks could be attached to each other using adhesive portion 11.

When mask 10 is positioned over the face of a patient as shown in FIG. 1, the periphery of the mask is pressed against the face so that adhesive 11 makes a temporary seal therearound. This seal prevents the ingress to the eyes of stray laser radiation during the procedure. If mask 10 is prewetted, cover 16 is removed so that the moistened pads 12 and 13 rest against the eyelids to prevent the eyes from drying out. However, if pre-moistened pads are not used, they should be moistened with a saline solution prior to adhering mask 10 to the patient's face.

While a presently preferred embodiment of the invention has been shown and described in particularity, it may be otherwise embodied within the scope of the appended claims.

What is claimed is:

1. A laser-beam resistant protective surgical eye mask for use during laser procedures conducted about the face comprising:
   a. a facial mask member configured and sized to cover the eyes and nose bridge of a patient, said member being made of a metal foil;
   b. a pair of eye pads secured on the inner surface of the facial member, said pads being made of moisture absorptive material;
   c. an adhesive portion positioned on the inner surface of the periphery of the facial member for temporarily sealing the facial member to the face of the patient; and
   d. a nonwettable cover member for said mask member having a shape and size substantially the same as the mask member and removably secured to said inner surface by the adhesive portion.

2. A protective eye mask as set forth in claim 1, wherein said facial mask member is made of aluminum foil and said eye pads are of a cotton gauze.

3. A protective eye mask as set forth in claim 1, wherein said eye pads are pre-moistened with a solution adaptable for radiation protective contact with a patient's eye and including a pair of nonwettable protective coverings sealingly and removably positioned over the respective pads to prevent said solution from evaporating prior to use.

* * * * *